(12) United States Patent
Thadani et al.

(10) Patent No.: US 8,350,047 B2
(45) Date of Patent: Jan. 8, 2013

(54) METHODS OF PREPARING SECONDARY CARBINAMINE COMPOUNDS WITH BORONIC ACIDS

(76) Inventors: Avinash N. Thadani, Windsor (CA); Bhartesh Dhudshia, Windsor (CA)

( * ) Notice: Subject to any disclaimer, the term of this patent is extended or adjusted under 35 U.S.C. 154(b) by 389 days.

(21) Appl. No.: 12/593,815

(22) PCT Filed: Mar. 28, 2008

(86) PCT No.: PCT/CA2008/000567
§ 371 (c)(1),
(2), (4) Date: Feb. 17, 2010

(87) PCT Pub. No.: WO2008/119161
PCT Pub. Date: Oct. 9, 2008

(65) Prior Publication Data
US 2010/0298572 A1    Nov. 25, 2010

Related U.S. Application Data

(60) Provisional application No. 60/909,000, filed on Mar. 30, 2007.

(51) Int. Cl.
C07D 213/02 (2006.01)
C07D 209/04 (2006.01)
C07B 57/00 (2006.01)
C07C 211/03 (2006.01)
C07C 209/00 (2006.01)

(52) U.S. Cl. ........ 546/329; 548/491; 564/303; 564/316; 564/397

(58) Field of Classification Search .................. 546/329; 548/491; 564/303, 316, 397
See application file for complete search history.

(56) References Cited

FOREIGN PATENT DOCUMENTS
CA    2249203    1/1998

OTHER PUBLICATIONS

H. C. Brown, U. S. Racherla and P. J. Pellechia, J. Org. Chem., 1990, 55, 1868.
Dhudshia, B., Tiburcio, J. and Thadani, A.N. Chem. Commun. 2005, 5551-5553.
S. Kobayashi, K. Hirano and M. Sugiura, J. Chem. Commun., 2005, 104-105.
M. Sugiura, K. Hirano and S. Kobayashi, J. Am. Chem. Soc., 2004, 126, 7182-7183.
Yamamoto, Y. and Asao, N., Chem. Rev., 1993, 93, 2207.

*Primary Examiner* — Rebecca Anderson
*Assistant Examiner* — Samantha Shterengarts
(74) *Attorney, Agent, or Firm* — Bereskin & Parr LLP/S.E.N.C.R.L., s.r.l.; Michael Fenwick

(57) ABSTRACT

The present application relates to novel methods for the preparation of secondary carbinamine compounds, particularly the preparation of secondary carbinamine compounds of the formula Ia, formula Ib or formula IV from aldehydes of the formula II and boronic acids of the formula III or formula V, in the presence of ammonia or an ammonia equivalent of the formula $NH_4^{+}X^{-}$.

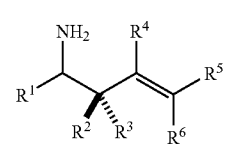

Ia

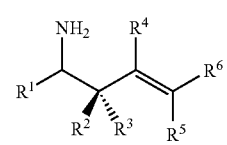

Ib

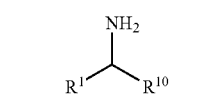

IV

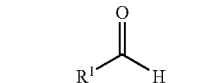

II

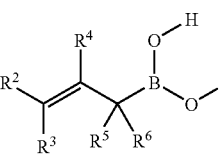

III

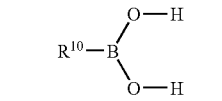

V

29 Claims, No Drawings

METHODS OF PREPARING SECONDARY CARBINAMINE COMPOUNDS WITH BORONIC ACIDS

This application is a national phase entry of PCT/CA2008/000567, filed Mar. 28, 2008, which claims priority from U.S. Provisional patent application Ser. No. 60/909,000 filed Mar. 30, 2007.

FIELD OF THE APPLICATION

The present application relates to novel methods for the preparation of secondary carbinamine compounds, particularly the preparation of secondary carbinamine compounds from aldehydes and boronic acids in the presence of ammonia.

BACKGROUND OF THE APPLICATION

Amines are one of the most common classes of organic molecules. They play important roles in a variety of areas, ranging from the pharmaceutical industry to plastics manufacturing.

Current methods for the synthesis of amines generally rely on multi-step processes that convert a variety of amine precursors to the amino ($NH_2$) functional group itself. To date, with the singular exception of two existing methodologies, there has been no general method for the direct synthesis of amines from ammonia. Since ammonia is an inexpensive bulk commodity chemical that is manufactured on a multi-ton scale annually, any process that allows for the direct use of ammonia for the introduction of the amino group is therefore highly desirable.

Research into the addition of allyl organometallics to carbonyl compounds and their derivatives continues to proceed unabated—a consequence of the fact that the resulting homoallylic products have proven to be valuable synthons [Denmark, S. E. and Almstead, N. G., *Modern Carbonyl Chemistry*, ed. Otera, J. Wiley-VCH, Weinheim, 2000, ch. 10; Yamamoto, Y. and Asao, N., *Chem. Rev.*, 1993, 93, 2207; and Roush, W. R., *Comprehensive Organic Synthesis*, ed. Trost, B. M., Fleming, I. and Heathcock, C. H., Pergamon, Oxford, 2nd edn., 1991, vol. 2, pp 1-53]. The majority of the research, however, has focused on the addition of allylboronic esters to aldehydes. For example, the reaction of

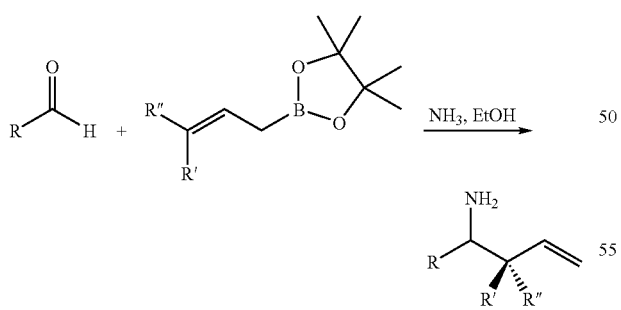

has previously been described by Kobayashi et al. [M. Sugiura, K. Hirano and S. Kobayashi, *J. Am. Chem. Soc.*, 2004, 126, 7182-7183; S. Kobayashi, K. Hirano and M. Sugiura, *J. Chem. Commun.*, 2005, 104-105].

A methodology for the diastereoselective addition of allyl- and crotyl-boronic acids to ketones in the presence of methanolic ammonia to produce tertiary homoallylic amines was recently reported [Dhudshia, B., Tiburcio, J. and Thadani, A. N. *Chem. Commun.* 2005, 5551-5553].

SUMMARY OF THE APPLICATION

Methods for the direct addition of a variety of nucleophiles to aldehydes in the presence of ammonia have been shown to afford the corresponding secondary carbinamine compounds in moderate to excellent yields under mild reaction conditions. The methods have been shown to be simple and efficient for the incorporation of ammonia into the carbinamine end-products.

Accordingly, the present application includes a method of preparing a secondary amine of the formula Ia and/or Ib:

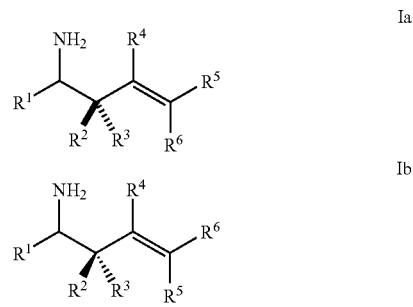

wherein
$R^1$ is selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alknyl, $C_{3-20}$cycloalkyl or $C_{3-20}$cycloalkoxy is optionally replaced with a heteromoiety selected from O, S, N, $NR^7$ and $NR^7R^8$;
$R^2$ to $R^6$ are independently selected from H, $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, the latter 9 groups being optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^7$ and $NR^7R^8$;
$R^7$ and $R^8$ are independently selected from H, $C_{1-20}$alkyl, $C_{3-20}$cycloalkyl, aryl and heteroaryl, the latter 4 groups being optionally substituted; comprising reacting a compound of formula II:

wherein $R^1$ is as defined for the compounds of formulae Ia and Ib, with a compound of formula III:

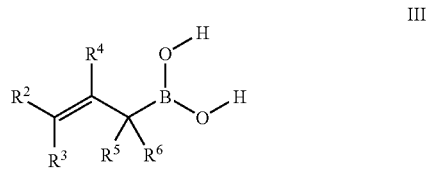

wherein $R^2$-$R^6$ are as defined for the compounds of formulae Ia and Ib, in the presence of ammonia $NH_3$ or an ammonia equivalent of the formula $NH_4^+X^-$, wherein X is an anionic counterion, and optionally isolating the amine of the formula Ia and/or Ib.

In another aspect, the present application relates to a method of preparing an amine of the formula IV:

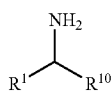
IV wherein
$R^1$ is selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^7$ and $NR^7R^8$;
$R^{10}$ is aryl or heteroaryl, both of which are optionally substituted; and
$R^7$ and $R^8$ are independently selected from H, $C_{1-20}$alkyl, $C_{2-20}$alkynyl, $C_{3-20}$cycloalkyl, aryl and heteroaryl, the latter 4 groups being optionally substituted; comprising reacting a compound of the formula II:

II wherein $R^1$ is as defined for the compounds of formula IV, with a compound of the formula V:

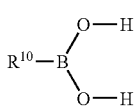
V wherein $R^{10}$ is as defined for the compound of formula IV, in the presence of ammonia $NH_3$ or an ammonia equivalent of the formula $NH_4^+X^-$, wherein X is an anionic counterion, and optionally isolating the amine of the formula IV.

It is an embodiment of the present application that the method of preparing the compounds of the formulae Ia, Ib and IV is performed in the presence of a catalyst, such as a transition metal catalyst. In a further embodiment, the catalyst comprises a chiral ligand and its use results in the preparation of enantiomerically enriched compounds of formulae Ia, Ib and IV.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DETAILED DESCRIPTION OF THE APPLICATION

Definitions

The term "$C_{1-n}$alkyl" as used herein means straight and/or branched chain alkyl groups containing from one to n carbon atoms and includes, depending on the identity of n, methyl, ethyl, propyl, isopropyl, t-butyl, pentyl, hexyl, heptyl, octyl, nonyl, decyl, undecyl, dodecyl, hexadecyl, octadecyl, icosyl and the like and wherein n is an integer representing the maximum number of carbon atoms in the group.

The term "$C_{3-n}$cycloalkyl" as used herein means saturated cyclic or polycyclic alkyl groups containing from three to n carbon atoms and includes, depending on the identity of n, cyclopropyl, cyclobutyl, cyclopentyl, cyclohexyl, cycloheptyl, cyclooctyl, cyclononyl, cyclodecyl, cycloundecyl, cyclododecyl, cyclohexadecyl, cyclooctadecyl, cycloicosyl, adamantyl and the like, and wherein n is an integer representing the maximum number of carbon atoms in the group.

The term "$C_{1-n}$alkoxy" as used herein means straight and/or branched chain alkoxy groups containing from one to n carbon atoms and includes, depending on the identity of n, methoxy, ethoxy, propoxy, isopropoxy, t-butoxy, pentoxy, hexoxy, heptoxy, octoxy, nonoxy, decoxy, undecoxy, dodecoxy, hexadecoxy, octadecoxy, icosoxy and the like, and wherein n is an integer representing the maximum number of carbon atoms in the group.

The term "$C_{3-n}$cycloalkoxy" as used herein means saturated cyclic or polycyclic alkoxy groups containing from three to n carbon atoms and includes, depending on the identity of n, cyclopropoxy, cyclobutoxy, cyclopentoxy, cyclohexoxy, cycloheptoxy, cyclooctoxy, cyclononoxy, cyclodecoxy, cycloundecoxy, cyclododecoxy, cyclohexadecoxy, cyclooctadecoxy, cycloicosoxy and the like, and wherein n is an integer representing the maximum number of carbon atoms in the group.

The term "$C_{2-n}$alkenyl" as used herein means straight and/or branched chain alkenyl groups containing from two to n carbon atoms and one to six double bonds and includes, depending on the identity of n, vinyl, allyl, 1-butenyl, 2-hexenyl and the like, and wherein n is an integer representing the maximum number of carbon atoms in the group.

The term "$C_{2-n}$alkynyl" as used herein means straight or branched chain alkynyl groups containing from 2 to n carbon atoms and one to six triple bonds and includes, depending on the identity of n, propargyl, 1-butynyl, 2-hexynyl and the like, and wherein n is an integer representing the maximum number of carbon atoms in the group.

The term "halo-substituted $C_{1-n}$alkyl" as used herein means straight or branched chain, saturated alkyl radicals containing from one to n carbon atoms in which one or all of the hydrogen atoms have been replaced with a halogen, in particular fluorine, and includes (depending on the identity of "n") trifluoromethyl, pentafluoroethyl, fluoromethyl and the like, where the variable n is an integer representing the largest number of carbon atoms in the alkyl radical.

The term "halo-substituted $C_{1-n}$alkoxy" as used herein means straight or branched chain, saturated alkoxy radicals containing from one to n carbon atoms in which one or all of the hydrogen atoms have been replaced with a halogen, in particular fluorine, and includes (depending on the identity of "n") trifluoromethoxy, pentafluoroethoxy, fluoromethoxy and the like, where the variable n is an integer representing the largest number of carbon atoms in the alkoxy radical.

The term "aryl" as used herein means a monocyclic or polycyclic carbocyclic ring system containing one or two aromatic rings and from 6 to 14 carbon atoms and includes phenyl, naphthyl, anthraceneyl, 1,2-dihydronaphthyl, 1,2,3,4-tetrahydronaphthyl, fluorenyl, indanyl, indenyl and the like.

The term "heteroaryl" as used herein means mono- or polycyclic heteroaromatic radicals containing from 5 to 14 atoms, of which 1 to 4 atoms are a heteroatom selected from nitrogen, oxygen and sulfur and includes furanyl, thienyl, pyrrolo, pyridyl, indolo, benzofuranyl and the like.

The term "halo" as used herein means halogen and includes chloro, fluoro, bromo and iodo.

The term "one or more" as used herein means that from one to the maximum allowable substitutions are allowed.

The term "optionally substituted" means unsubstituted or substituted. When a group is substituted it may be substituted one or more times, one to five times, one to three times, one to two times or one time.

The term "ammonia equivalent" as used here refers to a compound that reacts in situ to produce an equivalent of "$NH_3$" or ammonia.

The term "enantiomerically enriched" as used herein means a mixture of enantiomeric compounds that contains an excess of one enantiomer over the other(s).

The present application includes combinations of groups and substituents that are permitted and would provide a stable chemical entity according to standard chemical knowledge as would be known to those skilled in the art.

Methods of the Application

A new method for the preparation of secondary carbinamine compounds from the diastereoselective allylation and crotylation of aldehydes in the presence of ammonia has been developed. The method has been shown to provide the homoallylic amines in high yields through simple acid-base extraction.

Accordingly, the present application relates to a method of preparing a secondary amine of the formula Ia and/or Ib:

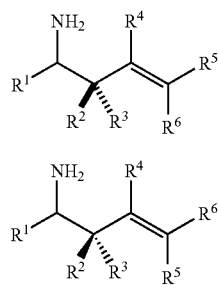

wherein
$R^1$ is selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alknyl, $C_{3-20}$cycloalkyl or $C_{3-20}$cycloalkoxy is optionally replaced with a heteromoiety selected from O, S, N, $NR^7$ and $NR^7R^8$;

$R^2$ to $R^6$ are independently selected from H, $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, the latter 9 groups being optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^7$ and $NR^7R^8$;

$R^7$ and $R^8$ are independently selected from H, $C_{1-20}$alkyl, $C_{3-20}$cycloalkyl, aryl and heteroaryl, the latter 4 groups being optionally substituted;

comprising reacting a compound of formula II:

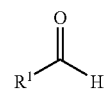

wherein $R^1$ is as defined for the compounds of formula Ia and Ib, with a compound of formula III:

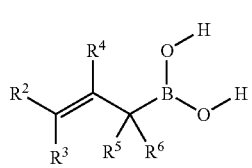

wherein $R^2$-$R^6$ are as defined for the compounds of formulae Ia and Ib, in the presence of ammonia $NH_3$ or an ammonia equivalent of the formula $NH_4^+X^-$, wherein X is an anionic counterion, and optionally isolating the amine of the formulae Ia and/or Ib.

It is an embodiment of the application that the compounds of formulae Ia, Ib and II include those in which $R^1$ is selected from $C_{1-10}$alkyl, $C_{3-8}$cycloalkyl, aryl, and heteroaryl, all of which are optionally substituted. In another embodiment of the application, one or more of the carbons in $C_{1-10}$alkyl or $C_{3-8}$cycloalkyl is optionally replaced with a heteromoiety selected from O, S, N, $NR^7$ and $NR^7R^8$, in which $R^7$ and $R^8$ are independently selected from H and $C_{1-6}$alkyl. Suitably, one or more of the carbons in $C_{1-18}$alkyl or $C_{3-8}$cycloalkyl is optionally replaced with a heteroatom selected from O and S.

It is another embodiment of the application that the optional substituents on $R^1$ in the compounds of the formulae Ia, Ib and II are independently selected from one or more of OH, halo, CN, $NO_2$, $C_{1-6}$alkyl, halo-substituted $C_{1-6}$alkyl, $C_{1-6}$alkoxy, halo-substituted $C_{1-6}$alkoxy, $C_{2-8}$alkenyl, $C_{2-8}$alkenyloxy, aryl, aryloxy, aryl($C_{1-4}$alkoxy), heteroaryl, heteroaryloxy, heteroaryl($C_{1-4}$alkoxy), $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl. Particularly, in an embodiment of the application, the optional substituents on $R^1$ in the compounds of the formulae Ia, Ib and II are independently selected from one to three of OH, F, Cl, Br, CN, $NO_2$, $CF_3$, $OCF_3$, $C_{1-4}$alkyl, $C_{1-4}$alkoxy, phenyl, benzyl, benzyloxy and $C(O)OC_{1-4}$alkyl.

It is an embodiment of the application that $R^2$ to $R^6$ in the compounds of the formulae Ia, Ib and III are independently selected from H, $C_{1-10}$alkyl, $C_{3-12}$cycloalkyl, aryl and heteroaryl, the latter 4 groups being optionally substituted. In another embodiment of the application, one or more of the carbons in $C_{1-10}$alkyl or $C_{3-10}$cycloalkyl is optionally replaced with a heteromoiety selected from O, S, N, $NR^7$ and $NR^7R^8$, in which $R^7$ and $R^8$ are independently selected from H and $C_{1-6}$alkyl. Suitably, one or more of the carbons in $C_{1-10}$alkyl or $C_{3-8}$cycloalkyl is optionally replaced with a heteroatom selected from O and S. In a particular embodiment of the application, $R^2$ to $R^6$ in the compounds of the formulae Ia, Ib and III are independently selected from H and $C_{1-6}$alkyl. In a more particular embodiment of the application, $R^2$ to $R^6$ in the compounds of the formulae Ia, Ib and III are independently selected from H and methyl.

In another embodiment of the application, the optional substituents on $R^2$ to $R^6$ in the compounds of the formulae Ia, Ib and III are independently selected from one or more of OH, halo, CN, $NO_2$, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, aryl, aryloxy, aryl($C_{1-4}$alkoxy), heteroaryl, heteroaryloxy, heteroaryl($C_{1-4}$alkoxy), $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

In an embodiment of the application, the method of preparing compounds of the formulae Ia and/or Ib is performed in the presence of ammonia. In yet another embodiment of the application, the method of preparing compounds of the formulae Ia and/or Ib is performed in the presence of an ammonia salt $NH_4^+X^-$ in which X is an anionic counterion. In a further embodiment of the application, X is selected from halo, $R^9COO$, $R^9SO_4$ and $BF_4$, in which $R^9$ is selected from $C_{1-10}$alkyl, $C_{3-20}$cycloalkyl, aryl and heteroaryl, all of which are optionally substituted. In an embodiment of the application, X is Cl or Br. In a still further embodiment of the application, the optional substituents on $R^9$ are independently selected from one or more of OH, halo, CN, $NO_2$, phenyl, benzyl, $C_{1-6}$alkoxy, halo-substituted $C_{1-6}$alkoxy, $C_{1-6}$alkyl, halo-substituted $C_{1-6}$alkyl, $C_{2-6}$alkenyl, $C_{2-6}$alkenyloxy, $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

In an embodiment of the application, the method of preparing compounds of formulae Ia and/or Ib is performed in a suitable solvent. More particularly, the solvent is selected from selected from selected from methanol, ethanol, propanol, butanol, toluene, tetrahydrofuran, acetonitrile, benzene, dioxane, methylene chloride, liquid ammonia, ionic liquids and mixtures thereof.

In an embodiment of the application, the method of preparing compounds of formulae Ia and/or Ib is performed by combining an alcoholic solution of ammonia, or an ammonia equivalent in a suitable solvent, with the compound of formula II. The ammonia or ammonia equivalent is suitably used in molar excess amounts, for example about 5 to about 20 molar equivalents, relative to the amount of the compound of formula II. Once the ammonia or ammonia equivalent has reacted with the compound of formula II for a sufficient period of time (determinable by a person skilled in the art, for example by following the reaction using thin layer chromatography and observing the disappearance of the compound of formula II), the compound of formula III may be added to the combined solution of ammonia or ammonia equivalent and compound of formula II. The compound of formula III may be used in molar excess amounts, for example about 1.1 to about 5 molar equivalents, suitably about 1.2 to 2.5 molar equivalents, relative to the amount of the compound of formula II.

It is an embodiment of the application that the method of preparing compounds of formulae Ia and/or Ib is performed at room temperature or above or below room temperature, for example, at a temperature of from −40° C. to +100° C., suitably from 0° C. to 50° C., more suitably from 10° C. to 30° C. In an embodiment of the application, the method is performed at room temperature.

A person skilled in the art would appreciate that the reaction conditions, including for example, temperature, time and reactant ratios, may vary depending on a number of variables, including, but not limited to, the structure of the starting materials (compounds of formulae II and III), the solvent, presence or absence of a catalyst (vide supra) and the reaction pressure. A person skilled in the art would be able to optimize the reaction conditions to obtain the best yields and overall performance of the reaction based on the results presented herein and methods known in the art. Reaction progress may be monitored using known techniques, for example, thin layer chromatography, high performance liquid chromatography and/or NMR spectroscopy, to determine optimum reaction conditions.

The compounds of the formulae Ia and/or Ib may optionally be isolated using standard methods known in the art, for example, by acid/base extraction methods. Further purification steps may be performed, for example, chromatography, and if $R^2$ and $R^3$ are different, chiral resolution. Chiral resolution of enantiomers may be performed, for example, by forming chiral esters or salts, followed by separation of the diastereomers using crystallization or chromatographic techniques, and liberation of the free amine.

A new method for the preparation of secondary carbinamine compounds from the diastereoselective arylation of aldehydes in the presence of ammonia has also been developed. The method has been shown to provide the aryl amines in high yields through simple acid-base extraction.

Accordingly, in another aspect, the present application relates to a method of preparing an amine of the formula IV:

IV wherein
$R^1$ is selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^7$ and $NR^7R^8$;
$R^{10}$ is aryl or heteroaryl, both of which are optionally substituted; and
$R^7$ and $R^8$ are independently selected from H, $C_{1-20}$alkyl, $C_{2-20}$alkynyl, $C_{3-20}$cycloalkyl, aryl and heteroaryl, the latter 4 groups being optionally substituted;
comprising reacting a compound of the formula II:

II wherein $R^1$ is as defined for the compounds of formula IV, with a compound of the formula V:

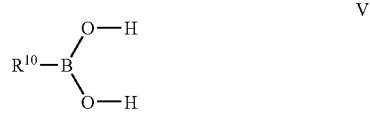

V wherein $R^{10}$ is as defined for the compound of formula IV, in the presence of ammonia $NH_3$ or an ammonia equivalent of the formula $NH_4^+X^-$, wherein X is an anionic counterion, and optionally isolating the amine of the formula IV.

It is an embodiment of the application that $R^1$ in the compounds of the formulae II and IV is selected from $C_{1-10}$alkyl, aryl and heteroaryl, all of which are optionally substituted. In another embodiment of the application, one or more of the carbons in $C_{1-10}$alkyl is optionally replaced with a heteromoiety selected from O, S, N, $NR^7$ and $NR^7R^8$, in which $R^7$ and $R^8$ are independently selected from H and $C_{1-6}$alkyl. Suitably, one or more of the carbons in $C_{1-10}$alkyl is optionally replaced with a heteroatom selected from O and S.

In an embodiment of the application, the optional substituents on $R^1$ in the compounds of the formulae II and IV are independently selected from one or more of OH, halo, CN, $NO_2$, $C_{1-6}$alkyl, halo-substituted alkyl, $C_{1-6}$alkoxy, halo-substituted alkoxy, $C_{2-6}$alkenyl, $C_{2-6}$alkenyloxy, aryl, aryloxy, aryl($C_{1-4}$alkoxy), heteroaryl, heteroaryloxy, heteroaryl($C_{1-4}$alkoxy), $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl. More particularly, in an embodiment of the application, the optional substituents on $R^1$ in the compounds of the formulae II and V are independently selected from one to three of OH, F, Cl, Br, CN, $NO_2$, $CF_3$, $OCF_3$, $C_{1-4}$alkyl, $C_{1-4}$alkoxy, phenyl, benzyl, benzyloxy and $C(O)OC_{1-4}$alkyl.

It is an embodiment of the application that $R^{10}$ in the compounds of the formulae IV and V is selected from phenyl, naphthyl, anthraceneyl, 1,2-dihydronaphthyl, 1,2,3,4-tetrahydronaphthyl, fluorenyl, indanyl, indenyl, furanyl, thienyl, pyrrolo, pyridyl, indolo and benzofuranyl, all of which are optionally substituted. In a particular embodiment of the application, $R^{10}$ in the compounds of the formulae IV and V is optionally substituted phenyl.

In an embodiment of the application, the optional substituents on $R^{10}$ in the compounds of the formulae IV and V are independently selected from one or more of OH, halo, CN, $NO_2$, $C_{1-6}$alkyl, halo-substituted alkyl, $C_{1-6}$alkoxy, halo-substituted alkoxy, $C_{2-6}$alkenyl, $C_{2-6}$alkenyloxy, aryl, aryloxy, aryl($C_{1-4}$alkoxy), heteroaryl, heteroaryloxy, heteroaryl($C_{1-4}$alkoxy), $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl. Particularly, in an embodiment of the application, the optional substituents on $R^{10}$ in the compounds of the formulae IV and V are independently selected from on to three of OH, F, Cl, Br, CN, $NO_2$, $CF_3$, $OCF_3$, $C_{1-4}$alkyl, $C_{1-4}$alkoxy, phenyl, benzyl, benzyloxy and $C(O)OC_{1-4}$alkyl.

In an embodiment of the application, the method of preparing compounds of formula IV is performed in the presence of ammonia. In yet another embodiment of the application, the method of preparing compounds of formula IV is performed in the presence of an ammonia salt $NH_4^+X^-$ in which X is an anionic counter ion. In a further embodiment of the application, X is selected from halo, $R^9COO$, $R^9SO_4$ and $BF_4$, in which $R^9$ is selected from $C_{1-10}$alkyl, $C_{3-20}$cycloalkyl, aryl and heteroaryl, all of which are optionally substituted. In an embodiment of the application, X is Cl or Br. In a still further embodiment of the application, the optional substituents on $R^9$ are independently selected from one or more of OH, halo, CN, $NO_2$, phenyl, benzyl, $C_{1-6}$alkoxy, halo-substituted alkoxy, $C_{1-6}$alkyl, halo-substituted alkyl, $C_{2-6}$alkenyl, $C_{2-6}$alkenyloxy, $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

In an embodiment of the application, the method of preparing compounds of formula IV is performed in a solvent. More particularly, the solvent is selected from selected from methanol, ethanol, propanol, butanol, toluene, tetrahydrofuran, acetonitrile, benzene, dioxane, methylene chloride, liquid ammonia, ionic liquids and mixtures thereof.

In an embodiment of the application, the method of preparing compounds of formula IV is performed by combining an alcoholic solution of ammonia, or an ammonia equivalent in a suitable solvent, with the compound of formula II. The ammonia or ammonia equivalent is suitably used in molar excess amounts, for example about 5 to about 20 molar equivalents, relative to the amount of the compound of formula II. Once the ammonia or ammonia equivalent has reacted with the compound of formula II for a sufficient period of time (determinable by a person skilled in the art, for example by following the reaction using thin layer chromatography and observing the disappearance of the compound of formula II), the compound of formula III may be added to the combined solution of ammonia or ammonia equivalent and compound of formula II. The compound of formula V may be used in molar excess amounts, for example about 1.1 to about 5 molar equivalents, suitably about 1.2 to 2.5 molar equivalents, relative to the amount of the compound of formula II.

In another embodiment of the present application, the method of preparing compounds of formula IV is performed at a temperature of from about −40° C. to about +150° C. More suitably, in an embodiment of the application, the method is performed at a temperature of from about +50° C. to about +120° C. It is an embodiment of the application that the method is performed at a temperature of about 80° C.

A person skilled in the art would appreciate that the reaction conditions, including for example, temperature, time and reactant ratios, may vary depending on a number of variables, including, but not limited to, the structure of the starting materials (compounds of formulae II and V), the solvent, presence or absence of a catalyst and the reaction pressure. A person skilled in the art would be able to optimize the reaction conditions to obtain the best yields and overall performance of the reaction based on the results presented herein and methods known in the art. Reaction progress may be monitored using known techniques, for example, thin layer chromatography, high performance liquid chromatography and/or NMR spectroscopy, to determine optimum reaction conditions.

The compounds of the formula IV may optionally be isolated using standard methods known in the art, for example, by acid/base extraction methods. Further purification steps may be performed, for example, chromatography, and if $R^1$ and $R^{10}$ are different, chiral resolution. Chiral resolution of enantiomers may be performed, for example, by forming chiral esters or salts, followed by separation of the diastereomers using crystallization or chromatographic techniques, and liberation of the free amine.

It is an embodiment of the application that the methods for preparing compounds of formula Ia, Ib and/or IV are performed in the presence of a catalyst, in particular a transition metal catalyst. Particularly, in an embodiment of the application, the catalyst is any of the well-known transition metal catalysts. In a further embodiment of the application, the metal is selected from rhodium, ruthenium, iridium, copper, platinum, palladium and nickel. In a still further embodiment of the application, the metal is rhodium. The catalyst may be included in the method, for example, by adding it along with the compound of formula III or V, either by a separate addition or in a combined solution with the compound of formula III or V.

In an embodiment of the present application, when a catalyst is used, it is added in amounts of about 1 mol % to about 20 mol %, suitably about 5 mol % to about 10 mol %, based on the amount of the aldehyde.

In another embodiment of the application, the metal catalyst possesses at least one chiral or achiral ligand. In another embodiment, the ligand is a phosphine, diphosphine, aminophosphine, carbene, amine or oxazoline ligand. Transition metal catalysts containing chiral ligands are well known in the art and include those used for stereoselective hydrogenations, transmetalation and other bond forming reactions [a] *Transition metals for organic synthesis*, ed. M. Beller and C. Bolm, Wiley-VCH, New York, 2nd edn, 2005; b) J. Tsuji in *Transition metal reagents and catalysts: innovations in organic synthesis*, John Wiley & Sons, New York, 2000]. By performing the methods described herein in the presence of a chiral catalyst, stereoselective additions of the compounds of formula II to the compounds of formula III, or the compounds of formulae II to the compounds of formula V, are achieved. Accordingly, compounds of formulae Ia, Ib and IV may be prepared in enantioselective and/or diastereoselective manner. In an embodiment, when a transition metal catalysts comprising a chiral ligand is used, an enantiomerically or diasteromerically enriched compound is obtained, i.e. one enantiomer or diastereomer will be present in an amount greater than 50%. In a further embodiment, one enantiomer or diastereomer will be present in an amount greater than 60%. In another embodiment, one enantiomer or diastereomer will be present in an amount greater than 70%. In a further embodiment, one enantiomer or diastereomer will be present in an amount greater than 80%. In yet a further embodiment, one enantiomer or diastereomer will be present in an amount greater than 90%. In another embodiment, one enantiomer or diastereomer will be present in an amount greater than 95%. In an embodiment, one enantiomer or diastereomer will be present in an amount greater than 99%.

The following non-limiting examples are illustrative of the present application:

EXAMPLES

Materials and Methods

All reagents were used as received (Aldrich, Acros, Strem). Methanol was dried over magnesium methoxide and distilled prior to use. Allyl (E)- and (Z)-crotylboronic acid in anhydrous methanol (2 M solution) were prepared just prior to use (exact molarities were confirmed by titration with benzaldehyde) [H. C. Brown, U. S. Racherla and P. J. Pellechia, *J. Org. Chem.*, 1990, 55, 1868].

Melting points were uncorrected and were measured on a Fisher-Johns melting point apparatus. $^1$H and $^{13}$C NMR were recorded at 300 or 500 MHz and 75 or 125 MHz respectively on a Bruker Spectrospin 300 or 500 MHz spectrometer. Proton chemical shifts were internally referenced to the residual proton resonance in CDCl$_3$ (δ 7.26). Carbon chemical shifts were internally referenced to the deuterated solvent signals in CDCl$_3$ (δ 77.00). Infrared spectra were obtained on a Bruker VECTOR22FT-IR spectrometer. HRMS-Cl and HRMS-ESI were performed on a Waters/Micromass GCT time-of-flight mass spectrometer and a Waters/Micromass Q-TOF Global quadrupole time-of-flight mass spectrometer respectively.

Example 1

General Procedure for the Allylation of Aldehydes with Allylboronic Acid in the Presence of Ammonia A solution of ammonia (ca. 7N in MeOH, 0.75 mmol, ca. 10 equiv.) was added to the aldehyde (1) (0.5 mmol). The resulting solution was stirred for 15 minutes at room temperature, followed by the addition of a freshly prepared solution of allylboronic acid (2) (2M in MeOH, 0.4 mL, 0.80 mmol) dropwise over 5 minutes. The reaction mixture was subsequently stirred for 1 hour at room temperature. The volatiles were removed in vacuo and the residue re-dissolved in Et$_2$O (15 mL). Aqueous HCl (1N, 15 mL) was then added dropwise to the residue. The biphasic mixture was vigorously shaken, and the layers were separated. The acidic aqueous layer was washed with Et$_2$O (3×15 mL), and made basic by the addition of solid NaOH (ca. 5 g). The aqueous layer was then extracted with CH$_2$Cl$_2$ (3×15 mL). The combined organic extracts were dried with Na$_2$SO$_4$, filtered and concentrated in vacuo to afford the desired secondary carbinamine (3). Table 1 summarizes the various aldehydes that were converted to carbinamines and the respective yields.

(i) 1-(Benzyloxy)pent-4-en-2-amine (3a)

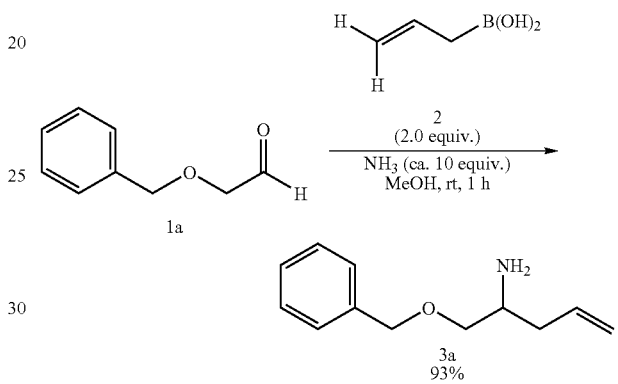

3a isolated as a clear, colorless oil: $^1$H NMR (CDCl$_3$, 300 MHz) δ 7.32-7.20 (5H, m), 5.84-5.67 (1H, m), 5.12-5.00 (2H, m), 4.83 (2H, s), 3.41 (1H, dd, J=9.0, 4.5 Hz), 3.24 (1H, dd, J=9.0, 7.5 Hz), 3.08-2.97 (1H, m), 2.25-2.15 (1H, m), 2.08-1.94 (1H, m), 1.37 (2H, br s); $^{13}$C NMR (CDCl$_3$, 75 MHz) δ 138.09, 134.98, 128.10, 127.35, 127.32, 117.16, 75.07, 72.95, 50.15, 38.59; HRMS (ESI) m/z calcd. for C$_{12}$H$_{18}$NO (MH$^+$) 192.1388, found 192.1384.

(ii) 1-(4-Methoxyphenyl)but-3-en-1-amine (3b)

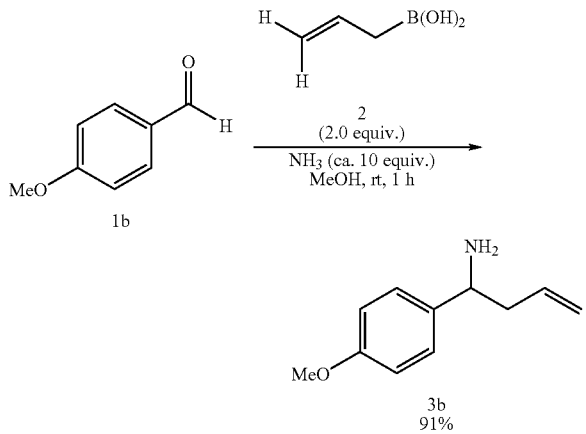

3b isolated as a clear, colorless oil: $^1$H NMR (CDCl$_3$, 300 MHz) δ 7.23 (2H, d, J=8.5 Hz), 6.84 (2H, d, J=8.5 Hz), 5.80-5.64 (1H, m), 5.13-5.00 (2H, m), 3.92 (1H, dd, J=8.0, 5.5 Hz), 3.76 (3H, s), 2.46-2.24 (2H, m), 1.48 (2H, br s); $^{13}$C NMR (CDCl$_3$, 75 MHz) δ 158.41, 137.89, 135.49, 127.18, 117.30, 113.60, 5.08, 54.65, 44.17; HRMS (CI) m/z calcd. for C$_{11}$H$_{16}$NO (MH$^+$) 178.1232, found 178.1227.

(iii) Undec-1-en-4-amine (3c)

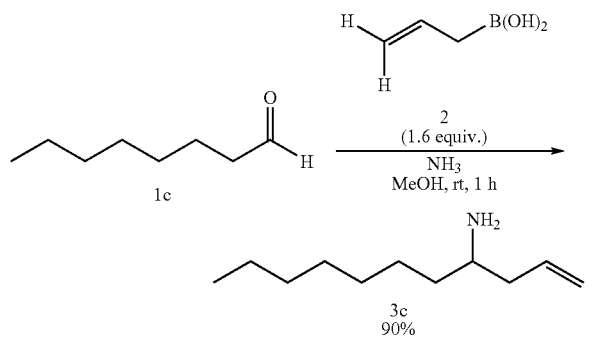

3c isolated as a clear, colorless oil: $^1$H NMR (CDCl$_3$, 300 MHz) δ 5.82-5.65 (1H, m), 5.09-4.98 (2H, m), 2.77-2.68 (1H, m), 2.23-2.12 (1H, m), 1.99-1.88 (1H, m), 1.43-1.15 (14H, m), 0.84 (3H, t, J=7.0 Hz); $^{13}$C NMR (CDCl$_3$, 75 MHz) δ 135.92, 117.06, 50.53, 42.56, 27.65, 31.77, 29.65, 29.23, 26.19, 22.58, 14.01; HRMS (CI) m/z calcd. for C$_{11}$H$_{24}$N (MH$^+$) 170.1909, found 170.1905.

(iv) 2,2-dimethylhex-5-en-3-amine (3d)

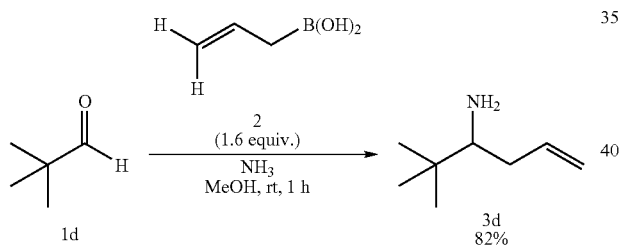

3d isolated as a clear, colorless oil: $^1$H NMR (CDCl$_3$, 500 MHz) δ 5.83-5.73 (1H, m), 5.06 (1H, dd, J=17.0, 1.5 Hz), 5.04 (1H, dd, J=10.0, 1.5 Hz), 2.42 (1H, dd, J=10.5, 2.5 Hz), 2.38-2.30 (1H, m), 1.76-1.67 (1H, m), 1.11 (2H, br s), 0.87 ((9H, s); $^{13}$C NMR (CDCl$_3$, 125 MHz) δ 137.71, 116.62, 59.47, 36.87, 26.09; HRMS (CI) m/z calcd. for C$_8$H$_{18}$N (MH$^+$) 128.1439, found 128.1437.

(v) 1-phenylhex-5-en-3-amine (3e)

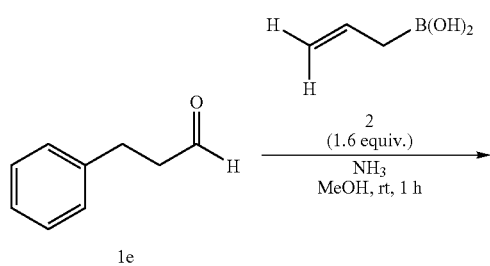

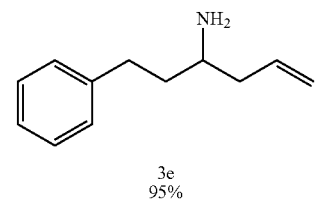

3e isolated as a clear, colorless oil: $^1$H NMR (CDCl$_3$, 300 MHz) δ 7.31-7.09 (5H, m), 5.87-5.69 (1H, m), 5.10 (1H, d, J=17.0 Hz), 5.09 (1H, d, J=11.0 Hz), 2.90-2.55 (3H, m), 2.33-2.20 (1H, m), 2.03 (1H, dt, J=13.5, 7.5 Hz), 1.83-1.55 (2H, m), 1.29 (2H, br s); $^{13}$C NMR (CDCl$_3$, 75 MHz) δ 142.18, 135.57, 128.29 (two signals overlapped), 125.70, 117.38, 50.10, 42.59, 39.31, 32.58.

(vi) 1-cyclohexylbut-3-en-1-amine (3f)

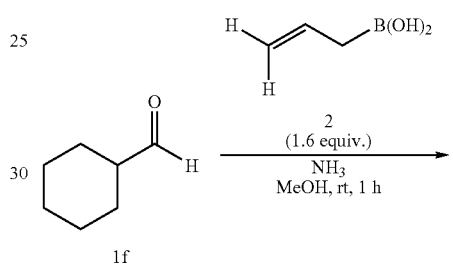

3f isolated as a clear, colorless oil: $^1$H NMR (CDCl$_3$, 300 MHz) δ 5.73 (1H, dddd, J=17.0, 10.5, 8.0, 6.0 Hz), 5.01 (1H, d, J=17.0 Hz), 4.99 (1H, d, J=10.5 Hz), 2.53-2.43 (1H, m), 2.25-2.15 (1H, m), 1.88 (1H, dt, J=13.5, 8.5 Hz), 1.64-1.42 (5H, m), 1.24-0.87 (8H, m); $^{13}$C NMR (CDCl$_3$, 75 MHz) δ 136.65, 116.94, 55.30, 43.47, 39.46, 29.68, 28.28, 26.62, 26.49, 26.37.

(vii) 1-(3-methoxyphenyl)but-3-en-1-amine (3g)

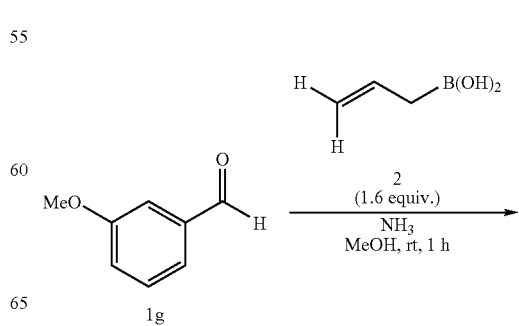

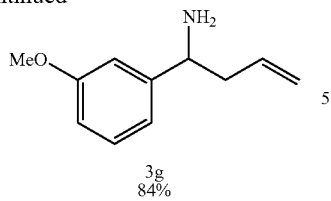

3g
84%

3g isolated as a low melting point solid: m.p.=30° C. (EtOAc); $^1$H NMR (CDCl$_3$, 300 MHz) δ 7.23 (1H, t, J=8.5 Hz), 6.95-6.87 (2H, m), 6.77 (1H, ddd, J=8.5, 2.5, 1.0 Hz), 5.74 (1H, dddd, J=17.0, 10.0, 8.0, 6.5 Hz), 5.11 (1H, J=17.0 Hz), 5.07 (1H, d, J=10.0 Hz), 4.00-3.92 (1H, m), 3.79 (3H, s), 2.45 (1H, dt, J=13.5, 6.0 Hz), 2.31 (1H, dt, J=13.5, 8.0 Hz), 1.57 (2H, br s); $^{13}$C NMR (CDCl$_3$, 75 MHz) δ 159.67, 147.60, 135.36, 129.32, 118.61, 117.56, 112.25, 111.84, 55.28, 55.13, 44.09.

(viii) 4-(1-aminobut-3-enyl)benzonitrile (3h)

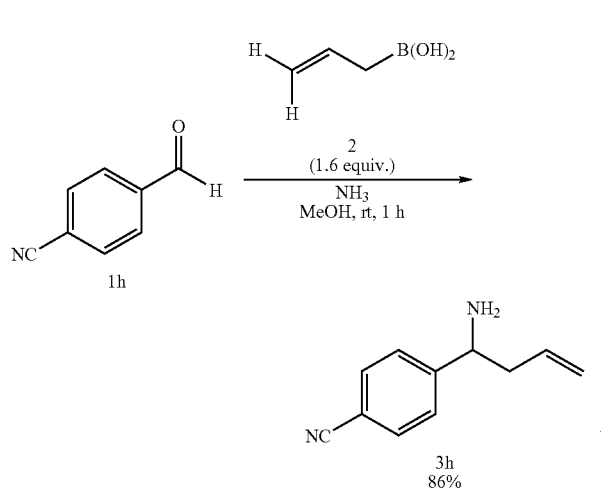

3h
86%

3h isolated as a clear, colorless oil: $^1$H NMR (CDCl$_3$, 300 MHz) δ 7.54 (1H, d, J=8.5 Hz), 7.41 (1H, d, J=8.5 Hz), 5.65 (1H, dddd, J=17.5, 10.5, 8.0, 6.5 Hz), 5.10-4.98 (2H, m), 4.01 (1H, dd, J=8.0, 5.5 Hz), 2.36 (1H, ddd, J=14.0, 6.5, 5.5 Hz), 2.26 (1H, dt, J=14.0, 8.0 Hz), 1.52 (2H, br s); $^{13}$C NMR (CDCl$_3$, 75 MHz) δ 151.35, 134.44, 132.22, 127.29, 118.98, 118.46, 110.67, 55.06, 44.03.

(ix) 1-(pyridin-2-yl)but-3-en-1-amine (3i)

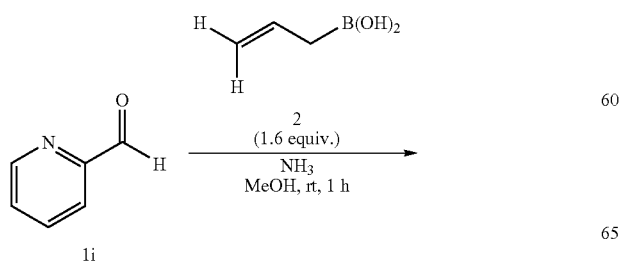

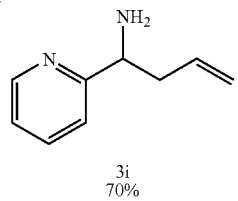

3i
70%

3i isolated as a clear, colorless oil: $^1$H NMR (CDCl$_3$, 300 MHz) δ 8.47 (1H, br s), 7.54 (1H, dt, J=7.5, 1.5 Hz), 7.22 (1H, d, J=8.0 Hz), 7.05 (1H, dd, J=7.5, 5.5 Hz), 5.69 (1H, dddd, J=17.5, 10.0, 7.5, 6.5 Hz), 5.01 (1H, d, J=17.5 Hz), 4.98 (1H, d, J=10.0 Hz), 3.96 (1H, t, J=7.5 Hz), 2.57-2.44 (1H, m), 2.30 (1H, dt, J=13.5, 8.0 Hz), 1.71 (2H, br s); $^{13}$C NMR (CDCl$_3$, 75 MHz) δ 163.95, 148.95, 136.21, 135.02, 121.71, 120.76, 117.54, 56.32, 43.09.

(x) 1-(1H-indol-3-yl)but-3-en-1-amine (3j)

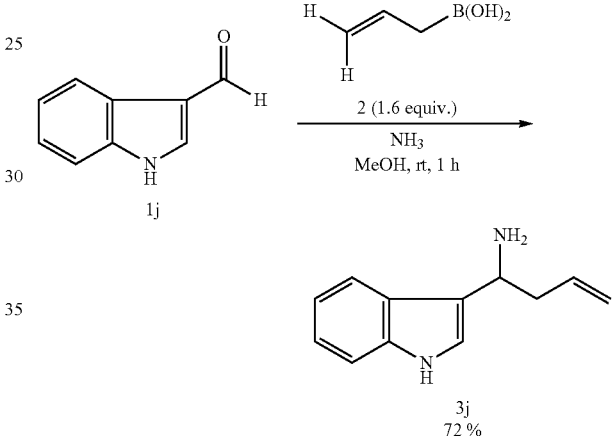

3j
72 %

3j isolated as a clear, colorless oil: $^1$H NMR (CDCl$_3$, 300 MHz) d8.94 (1H, br s), 7.73 (1H, d, J=7.5 Hz), 7.31 (1H, d, J=8.0 Hz), 7.24-7.10 (2H, m), 7.02 (1H, d, J=2.0 Hz), 5.96-5.80 (1H, m), 5.25-5.10 (2H, m), 4.41 (1H, dd, J=8.0, 5.0 Hz), 2.80-2.69 (1H, m), 2.60-2.47 (1H, m), 1.80 (2H, br s); $^{13}$C NMR (CDCl$_3$, 75 MHz) d 136.47, 135.83, 125.83, 121.77, 120.66, 120.26, 119.10, 118.95, 117.38, 111.29, 47.91, 42.98.

Discussion

The addition of allylboronic acid (2) to aldehydes, when first pretreated with ammonia, has been found to lead cleanly and efficiently to the formation of the corresponding secondary carbinamines under mild reaction conditions. As seen in Table 1, the resulting secondary carbinamines were easily isolated and uniformly obtained in high yields through standard acid-base extraction, and did not require any subsequent chromatographic purification.

Example 2

General Procedure for the Crotylation of Aldehydes with (E) or (Z)-Crotylboronic Acid in the Presence of Ammonia A solution of ammonia (ca. 7N in MeOH, 0.75 mmol, ca. 10 equiv.) was added to the aldehyde (1) (0.5 mmol). The resulting solution was stirred for 15 minutes at room temperature, followed by the addition of a freshly prepared solution of either (E) or (Z)-crotylboronic acid (4a) or (4b) (2M in MeOH, 0.4 mL, 0.80 mmol) dropwise over 5 minutes. The reaction mixture was subsequently stirred for 1 hour at room temperature. The volatiles were removed in vacuo and the residue re-dissolved in Et$_2$O (15 mL). Aqueous HCl (1N, 15 mL) was then added dropwise to the residue. The biphasic mixture was vigorously shaken, and the layers were separated. The acidic aqueous layer was washed with Et$_2$O (3×15 mL), and made basic by the addition of solid NaOH (ca. 5 g). The aqueous layer was then extracted with CH$_2$Cl$_2$ (3×15 mL). The combined organic extracts were dried with Na$_2$SO$_4$, filtered and concentrated in vacuo to afford the desired secondary carbinamine (5). Table 2 summarizes the various aldehydes that were converted to carbinamines using (E) or (Z)-crotylboronic acid and the respective yields and diastereomeric ratios (d.r.).

(i) (2S,3S)-1-(benzyloxy)-3-methylpent-4-en-2-amine (5a)

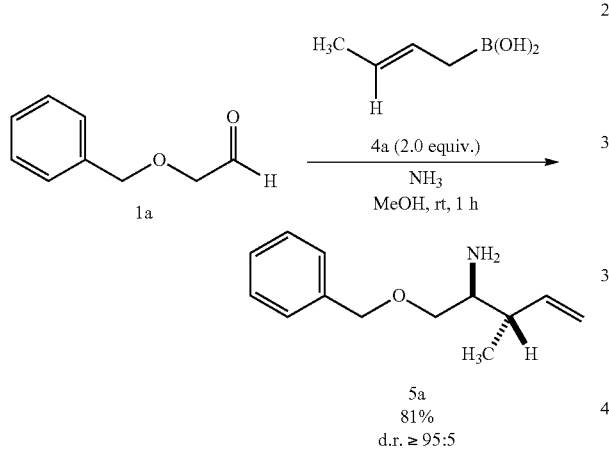

5a
81%
d.r. ≥ 95:5

5a isolated as a clear, colorless oil: $^1$H NMR (CDCl$_3$, 300 MHz) δ 7.35-7.22 (5H, m), 5.78-5.65 (1H, m), 5.09-5.00 (2H, m), 4.51 (2H, br s), 3.50 (1H, dd, J=9.0, 4.0 Hz), 3.32 (1H, dd, J=9.0, 7.5 Hz), 2.92-2.77 (1H, m), 2.23 (1H, hextet, J=7.0 Hz), 1.36 (2H, br s), 1.00 (3H, d, J=7.0 Hz); $^{13}$C NMR (CDCl$_3$, 75 MHz) δ 140.70, 138.27, 128.25, 127.52, 127.46, 115.34, 73.61, 73.16, 54.82, 41.15, 16.74; HRMS (Cl) m/z calcd. for C$_{13}$H$_{20}$NO (MH$^+$) 206.1545, found 206.1550.

(ii) (1S,2S)-1-(4-Methoxyphenyl)-2-methylbut-3-en-1-amine (5b)

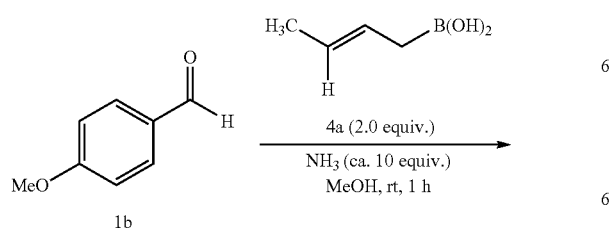

-continued

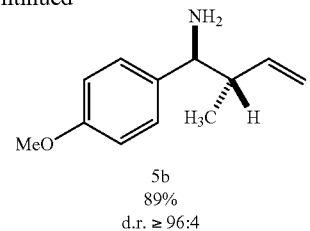

5b
89%
d.r. ≥ 96:4

5b isolated as a clear, colorless oil: $^1$H NMR (CDCl$_3$, 300 MHz) δ 7.20 (2H, d, J=8.5 Hz), 6.83 (2H, d, J=8.5 Hz), 5.71 (1H, ddd, J=17.5, 10.0, 8.5 Hz), 5.13 (1H, dd, J=17.5, 2.0 Hz), 5.07 (1H, dd, J=10.0, 2.0 Hz), 3.76 (3H, s), 3.56 (1H, d, J=8.0 Hz), 3.29 (1H, hextet, J=7.0 Hz), 1.48 (2H, br s), 0.78 (3H, d, J=7.0 Hz); $^{13}$C NMR (CDCl$_3$, 75 MHz) δ 158.46, 141.76, 136.54, 128.07, 115.47, 113.42, 59.86, 55.01, 46.35, 17.49; HRMS (Cl) m/z calcd. for C$_{13}$H$_{20}$NO (MH$^+$) 206.1545, found 206.1550.

(iii) (1S,2R)-1-(4-Methoxyphenyl)-2-methylbut-3-en-1-amine (5c)

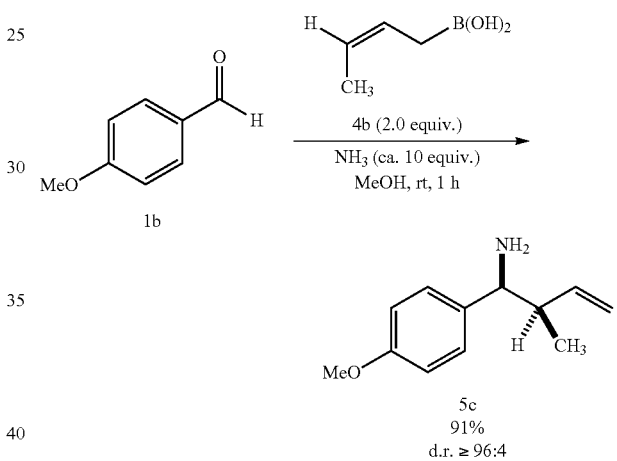

5c
91%
d.r. ≥ 96:4

(iv) (1S,2R)-1-(1H-indol-3-yl)-2-methylbut-3-en-1-amine (5d)

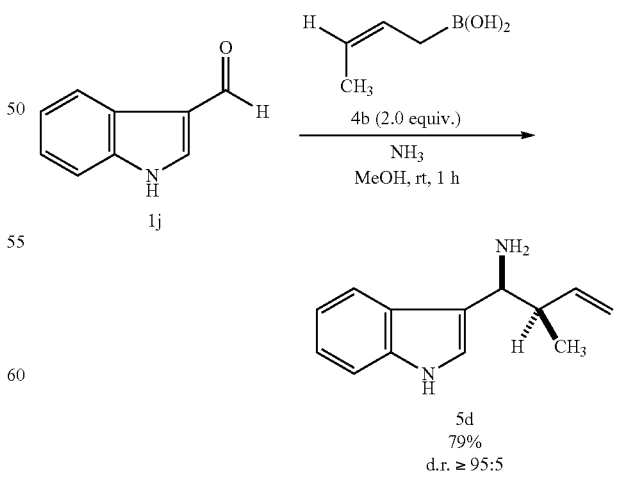

5d
79%
d.r. ≥ 95:5

5d isolated as a clear, colorless oil: $^1$H NMR (CDCl$_3$, 500 MHz) d 8.82 (1H, br s), 7.71 (1H, d, J=8.0 Hz), 7.32 (1H, d, J=8.0 Hz), 7.22 (1H, t, J=7.0 Hz), 7.16 (1H, t, J=7.0 Hz), 7.04

(1H, d, J=2.0 Hz), 5.94 (1H, ddd, J=17.5, 10.5, 7.0 Hz), 5.16 (1H, dd, J=17.5, 1.5 Hz), 5.10 (1H, dd, J=10.5, 1.5 Hz), 4.37 (1H, d, J=5.0 Hz), 2.78 (1H, J=5.5 Hz), 1.68 (2H, br s), 1.07 (3H, d, J=7.0 Hz); $^{13}$C NMR (CDCl$_3$, 125 MHz) d 141.75, 136.37, 126.40, 121.70, 121.59, 119.35, 119.18, 119.09, 114.61, 111.18, 52.87, 43.69, 14.72.

Discussion

The addition of (E) or (Z)-crotyltrifluoroborate (4a) or (4b) to aldehydes, when first pretreated with ammonia, has been found to lead cleanly and efficiently to the formation of the corresponding secondary carbinamines under mild reaction conditions as seen in Table 2. Excellent diastereoselectivities were observed with all the tested substrates, in which the (E)-crotyl reagent (4a) afforded the anti-homoallylic amine, and the (Z)-crotyl reagent (4b) afforded the syn-homoallylic amine. The resulting secondary carbinamines were easily isolated and uniformly obtained in high yields through standard acid-base extraction, and did not require any subsequent purification.

Example 3

General Procedure for the Rhodium-Catalyzed Addition of Aryl and Alkenylboronic Acids to Aldehydes in the Presence of Ammonia A saturated solution of ammonia in 1,4-dioxane (2 mL) was added to the aldehyde (6). To the resulting solution was added freshly prepared boronic acid (8) (1.0 mmol) and Rh(acac)(CO)$_2$ (12.9 mg, 0.05 mmol). Distilled water (0.4 mL) was then added to the solution and the reaction mixture was heated to 80° C. in a sealed tube for 16 h. The reaction mixture was then cooled to room temperature and the volatiles were removed in vacuo. The residue was dissolved in CH$_2$Cl$_2$ (20 mL) and washed with saturated aq. NaHCO$_3$ (10 mL). The organic layer was dried (Na$_2$SO$_4$), filtered and concentrated in vacuo to afford a yellow oil, which was then subjected to silica gel chromatography (EtOAc/hexanes/Et$_3$N) to afford the carbinamine (8). In some cases, the resulting carbinamine (8) was treated with HCl (1.0 M in Et$_2$O) to afford the corresponding hydrochloride salt. The salt was then isolated by filtration.

(i) (4-bromophenyl)(phenyl)methanamine (8a)

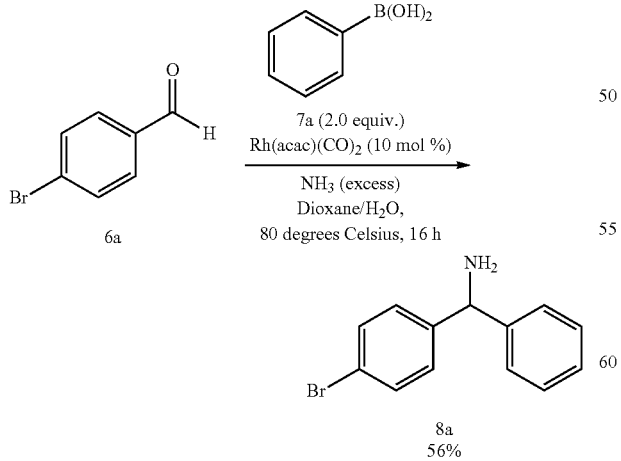

8a isolated as a clear, colourless oil. $^1$H NMR (CD$_3$OD, 300 MHz) d 7.55 (2H, d, J=8.5 Hz), 7.50-7.13 (7H, m), 5.48 (1H, s), 1.80 (2H, br s).

(ii) Phenyl(4-(trifluoromethyl)phenyl)methanaminium chloride (8b)

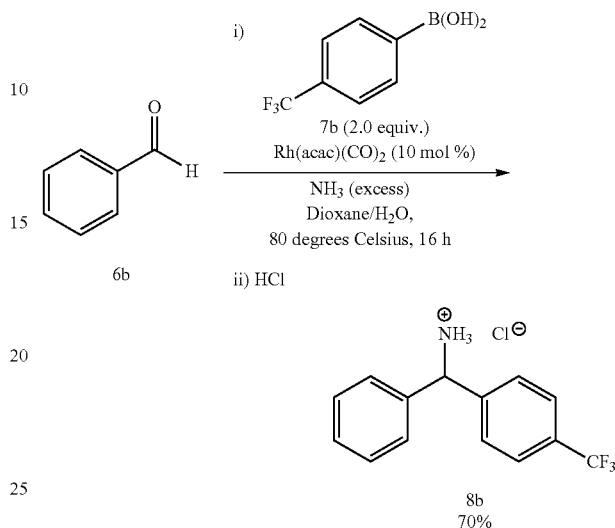

8b isolated as a white solid: mp=231-234° C.; $^1$H NMR (500 MHz, CD$_3$OD) δ 7.78 (2H, d, J=8.0 Hz), 7.64 (1H, s), 7.62 (1H, d, J=0.5 Hz), 7.51-7.41 (5H, m), 5.79 (1H, s); $^{13}$C NMR (125 MHz, CD$_3$OD) δ 143.04, 138.05, 132.31 (q, J=32.0 Hz), 130.73, 130.50, 129.33, 128.78, 127.46 (q, J=4.0 Hz), 59.04.

(iii) naphthalen-2-yl(p-tolyl)methanaminium chloride (8c)

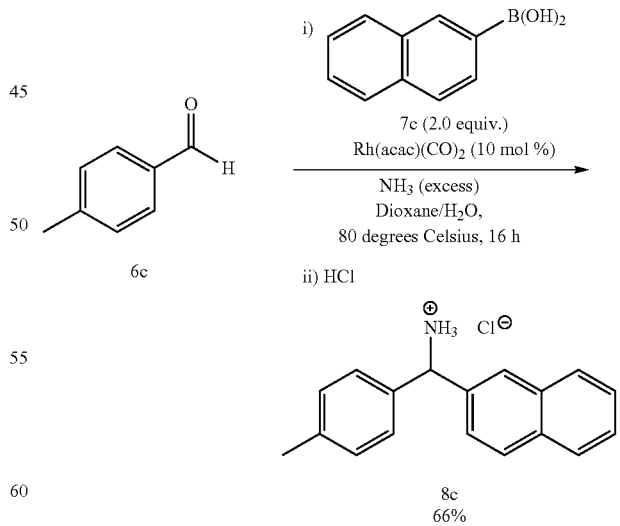

8c isolated as a white solid: mp=234-236° C.; $^1$H NMR (300 MHz, CD$_3$OD) δ 7.97-7.90 (4H, m), 7.60-7.56 (2H, m), 7.47 (1H, dd, J=9.0, 2.0 Hz), 7.38 (2H, d, J=8.5 Hz), 7.31 (2H, d, J=8.0 Hz), 5.80 (1H, s), 2.39 (3H, s); $^{13}$C NMR (75 MHz, CD$_3$OD) δ 138.90, 134.79, 134.24, 133.24, 129.52, 128.88, 127.94, 127.87, 127.46, 127.14, 126.73, 126.64, 125.86 124.38, 58.05, 19.83.

(iv) (4-chlorophenyl)(phenyl)methanaminium chloride (8d)

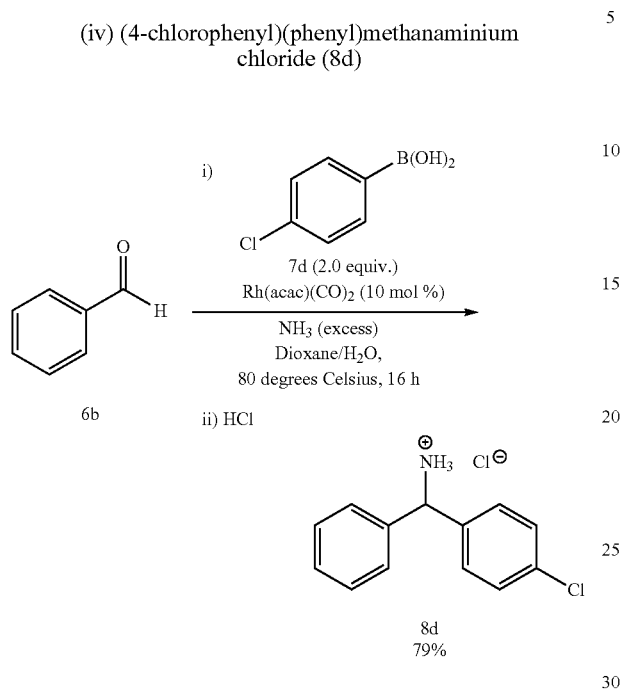

8d isolated as a white solid: m.p.=220-224° C.; $^1$H NMR (300 MHz, CD$_3$OD) δ 7.48 (9H, s), 5.71 (1H, s); $^{13}$C NMR (75 MHz, CD$_3$OD) δ 144.81, 136.92, 136.13, 134.51, 129.06, 128.97, 128.83, 128.74, 127.00, 120.26, 57.43.

Discussion:

The addition of aryl boronic acids (7) to aldehydes (6), when first pretreated with ammonia, led cleanly and efficiently to the formation of the corresponding secondary carbinamines under mild reaction conditions as seen in Table 3. The resulting secondary carbinamines were easily isolated and uniformly obtained in good yields.

Example 4

General Procedure for the Enantioselective Rhodium-Catalyzed Addition of Aryl- and Alkenylboronic Acids to Aldehydes in the Presence of Ammonia A saturated solution of ammonia in 1,4-dioxane (2 mL) was added to the aldehyde. To the resulting solution was added freshly prepared boronic acid (1.0 mmol), Rh(acac)(CO)$_2$ (6.5 mg, 0.025 mmol) and (2S,5S)-Duphos (8 mg, 0.025 mmol). Distilled and degassed water (0.4 mL) was then added to the solution and the reaction mixture was heated to 80° C. in a sealed tube for 16 h. The reaction mixture was then cooled to room temperature and the volatiles were removed in vacuo. The residue was dissolved in CH$_2$Cl$_2$ (20 mL) and washed with saturated aq. NaHCO$_3$ (10 mL). The organic layer was dried (Na$_2$SO$_4$), filtered and concentrated in vacuo to afford a yellow oil, which was then subjected to silica gel chromatography (EtOAc/hexanes/Et$_3$N) to afford the carbinamine (9). The enantioselectivities were measured by chiral HPLC. In some cases, the resulting carbinamine (9) was treated with HCl (1.0 Min Et$_2$O) to afford the corresponding hydrochloride salt. The salt was then isolated by filtration.

(i) (4-methoxyphenyl)(phenyl)methanamine (9a)

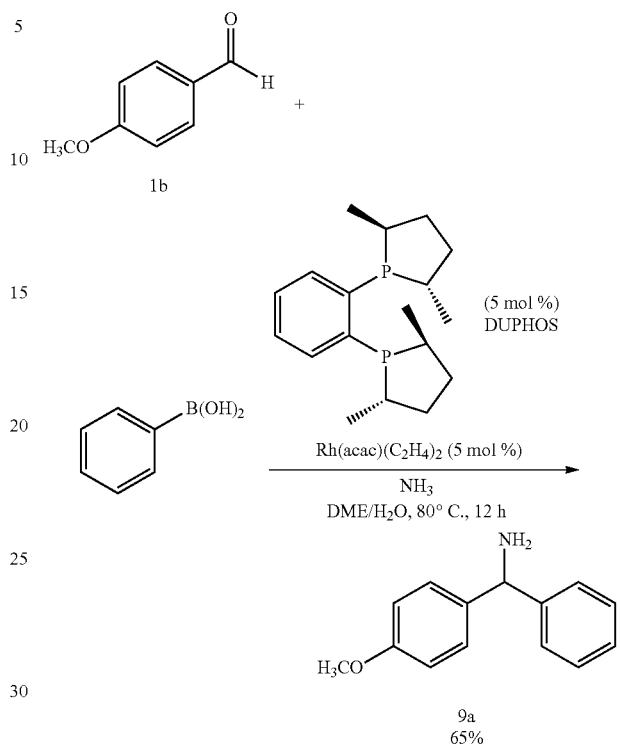

9a isolated as a clear, pale yellow oil: $^1$H NMR [300 MHz, (CD$_3$)$_2$SO]δ 7.40-7.10 (7H, m), 6.85 (2H, dd, J=7.0, 2.0 Hz), 5.02 (1H, s), 3.70 (3H, s), 2.08 (2H, br s); optical rotation $\alpha_D^{21}$=10.9° (c=1.00, MeOH)

(ii) (4-methoxyphenyl)(p-tolyl)methanaminium chloride (9b)

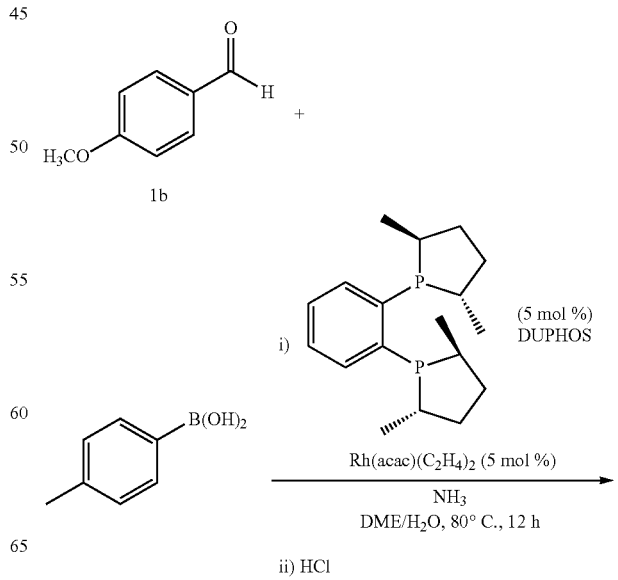

-continued
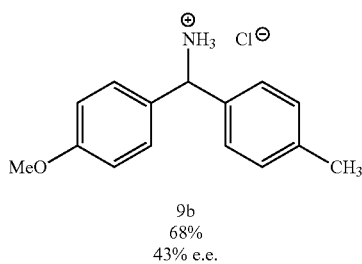
9b
68%
43% e.e.
9b was isolated as a white solid: m.p. (Et$_2$O)=257-260° C.; $^1$H NMR (300 MHz, CD$_3$OD) δ 7.50-7.39 (5H, m), 7.33-7.22 (4H, m), 5.60 (1H, s), 4.98 (3H, br s), 2.33 (3H, s); $^{13}$C NMR (75 MHz, CD$_3$OD) δ 140.23, 138.71, 135.62, 130.83, 130.27, 129.95, 128.33, 59.18, 21.11; optical rotation $\alpha_D^{21}$=65.7° (c=1.00, MeOH)
(iii) (4-fluorophenyl)(4-methoxyphenyl)methanamine (9c)
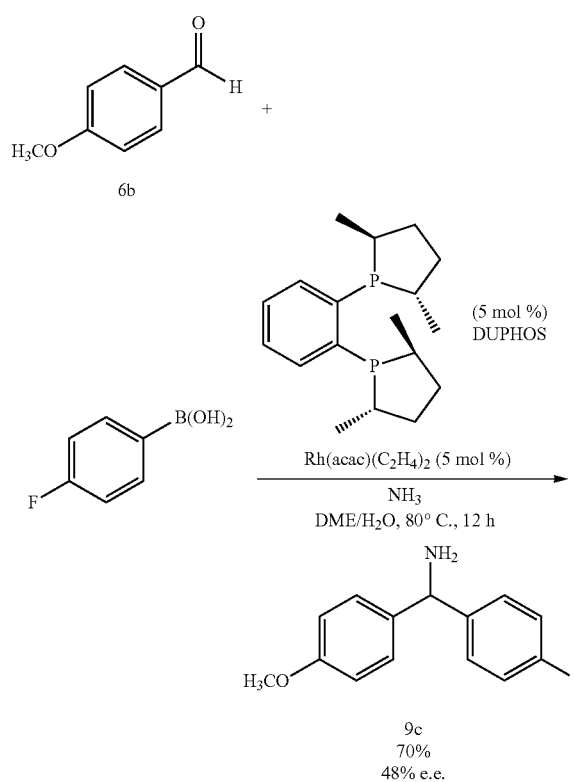
9c
70%
48% e.e.
(iv) (4-methoxyphenyl)(phenyl)methanamine (9d)
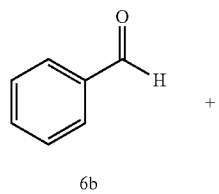
6b
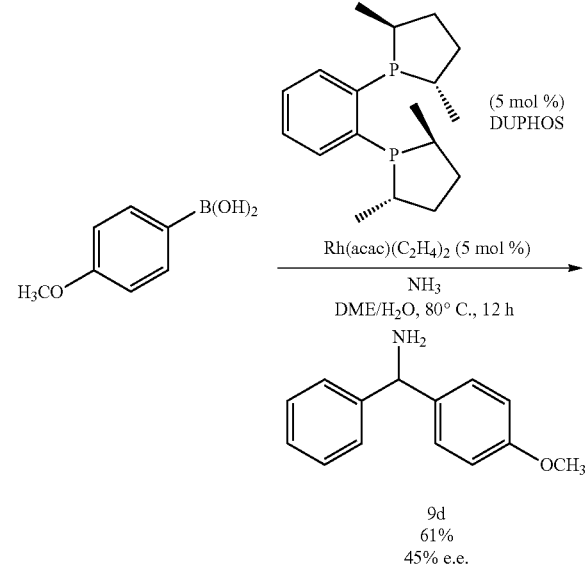
9d
61%
45% e.e.
(v) phenyl(p-tolyl)methanamine (9e)
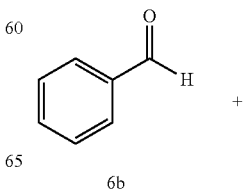
6b -continued

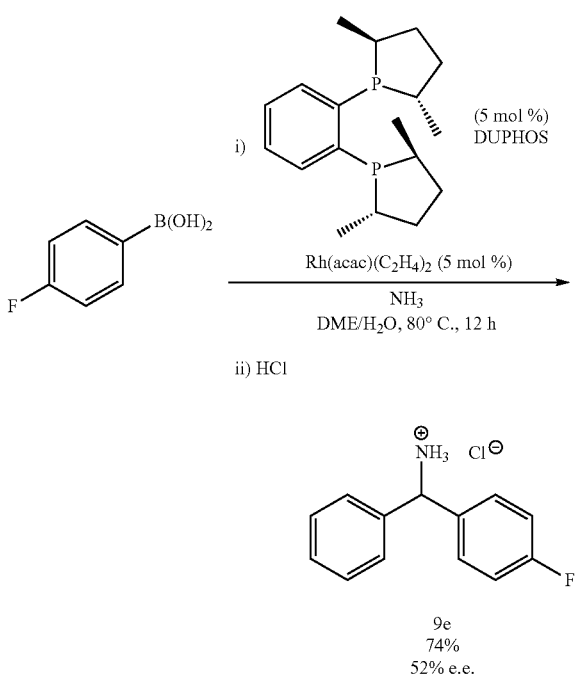

i) (5 mol %) DUPHOS

Rh(acac)(C₂H₄)₂ (5 mol %)
$\xrightarrow{\text{NH}_3}$
DME/H₂O, 80° C., 12 h ii) HCl 9e
74%
52% e.e.

9f isolated as a white solid: $^1$H NMR (400 MHz, CD₃OD) δ 7.50-7.42 (7H, m), 7.25-7.15 (2H, m), 5.72 (1H, s), 4.94 (3H, br s).

Discussion

The addition of aryl boronic acids to aldehydes in the presence of a rhodium catalyst and DUPHOS, when first pretreated with ammonia, has been found to lead cleanly and enantioselectively to the formation of the corresponding secondary carbinamines under mild reaction conditions as seen in Table 4. The resulting secondary carbinamines were easily isolated and uniformly obtained in good yields.

TABLE 1

Reaction of aldehydes with allylboronic acid in the presence of ammonia

| entry | R | yield (%) |
|---|---|---|
| 3a | PhCH₂OCH₂ | 93 |
| 3b | 4-CH₃OC₆H₄ | 91 |
| 3c | n-C₇H₁₅ | 90 |
| 3d | t-Bu | 82 |
| 3e | PhCH₂CH₂ | 95 |
| 3f | Cyclohexyl | 87 |
| 3g | 3-CH₃OC₆H₄ | 84 |
| 3h | 4-NCC₆H₄ | 86 |
| 3i | 2-Pyridyl | 70 |
| 3j | 3-Indolyl | 72 |

TABLE 2

Reaction of aldehydes with (E)- or (Z)-crotylboronic acids in the presence of ammonia 4a: R¹ = CH₃, R² = H
4b: R¹ = H, R² = CH₃

| entry | R | reagent | d. r. | yield (%) |
|---|---|---|---|---|
| 5a | PhCH₂OCH₂ | 4a | 95:5 | 81 |
| 5b | 4-CH₃OC₆H₄ | 4a | 96:4 | 89 |
| 5c | 4-CH₃OC₆H₄ | 4b | 96:4 | 91 |
| 5d | 3-Indolyl | 4b | 95:5 | 79 |

TABLE 3

Rhodium catalyzed addition of aryl boronic acids to aldehydes in the presence of ammonia

| entry | R¹ | R² | yield (%) |
|---|---|---|---|
| 8a | 4-BrC₆H₄ | Ph | 56 |
| 8b | Ph | 4-F₃CC₆H₄ | 70 |
| 8c | 4-CH₃C₆H₄ | 2-Naphthyl | 66 |
| 8d | Ph | 4-ClC₆H₄ | 79 |

TABLE 4

Rhodium catalyzed enantioselective addition of arylboronic acids to aldehydes in the presence of ammonia

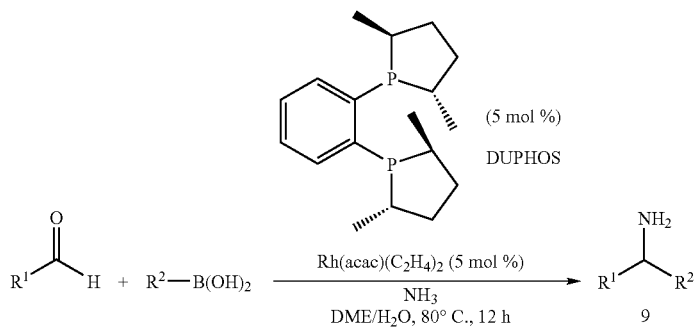

| entry | $R^1$ | $R^2$ | yield (%) | ee (%) |
|---|---|---|---|---|
| 9a | 4-MeOC$_6$H$_4$ | Ph | 65 | 39 |
| 9b | 4-MeOC$_6$H$_4$ | 4-CH$_3$C$_6$H$_4$ | 68 | 43 |
| 9c | 4-MeOC$_6$H$_4$ | 4-FC$_6$H$_4$ | 70 | 48 |
| 9d | Ph | 4-MeOC$_6$H$_4$ | 61 | 45 |
| 9e | Ph | 4-MeC$_6$H$_4$ | 64 | 49 |
| 9f | Ph | 4-FC$_6$H$_4$ | 74 | 52 |

We claim:

1. A method of preparing a secondary amine of the formula Ia and/or Ib:

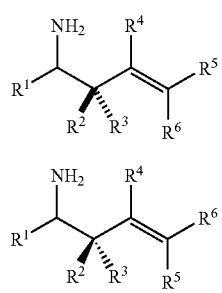

wherein $R^1$ is selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alknyl, $C_{3-20}$cycloalkyl or $C_{3-20}$cycloalkoxy is optionally replaced with a heteromoiety selected from O, S, N, NR$^7$ and NR$^7$R$^8$;

$R^2$ to $R^6$ are independently selected from H, $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, the latter 9 groups being optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, NR$^7$ and NR$^7$R$^8$;

$R^7$ and $R^8$ are independently selected from H, $C_{1-20}$alkyl, $C_{3-20}$cycloalkyl, aryl and heteroaryl, the latter 4 groups being optionally substituted;

comprising reacting a compound of formula II:

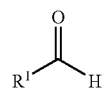

wherein $R^1$ is as defined for the compounds of formula Ia and Ib, with a compound of formula III:

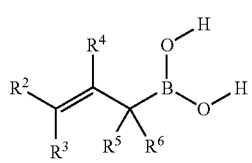

wherein $R^2$-$R^6$ are as defined for the compounds of formulae Ia and Ib, in the presence of ammonia NH$_3$ or an ammonia equivalent of the formula NH$_4^+$X$^-$, wherein X is an anionic counterion, and optionally isolating the amine of the formula Ia and/or Ib.

2. The method according to claim 1, wherein $R^1$ is selected from $C_{1-10}$alkyl, $C_{3-8}$cycloalkyl, aryl, and heteroaryl, all of which are optionally substituted and one or more of the carbons in $C_{1-10}$alkyl or $C_{3-8}$cycloalkyl is optionally replaced with a heteromoiety selected from O, S, N, NR$^7$ and NR$^7$R$^8$, in which R$^7$ and R$^8$ are independently selected from H and $C_{1-6}$alkyl.

3. The method according to claim 2, wherein one or more of the carbons in $C_{1-10}$alkyl or $C_{3-8}$cycloalkyl is optionally replaced with a heteroatom selected from O and S.

4. The method according to claim 1, wherein the optional substituents on R$^1$ in the compounds of the formulae Ia, Ib and II are independently selected from one or more of OH, halo, CN, NO$_2$, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, aryl, aryloxy, aryl($C_{1-4}$alkoxy), heteroaryl, heteroaryloxy, heteroaryl($C_{1-4}$alkoxy), $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

5. The method according to claim 4, wherein the optional substituents on $R^1$ in the compounds of the formulae Ia, Ib and II are independently selected from one to three of OH, F, Cl, Br, CN, $NO_2$, $CF_3$, $OCF_3$, $C_{1-4}$alkyl, $C_{1-4}$alkoxy, phenyl, benzyl, benzyloxy and $C(O)OC_{1-4}$alkyl.

6. The method according to claim 5, wherein the optional substituents on $R^1$ in the compounds of the formulae Ia, Ib and II are independently selected from one to three of F, Cl, Br, $C_{1-4}$alkoxy and benzyloxy.

7. The method according to claim 1, wherein $R^2$ to $R^6$ in the compounds of the formulae Ia, Ib and III are independently selected from H, $C_{1-10}$alkyl, $C_{3-12}$cycloalkyl, aryl and heteroaryl, the latter 4 groups being optionally substituted and one or more of the carbons in $C_{1-10}$alkyl or $C_{3-10}$cycloalkyl is optionally replaced with a heteromoiety selected from O, S, N, $NR^7$ and $NR^7R^8$, in which $R^7$ and $R^8$ are independently selected from H and $C_{1-6}$alkyl.

8. The method according to claim 7, wherein $R^2$ to $R^6$ in the compounds of the formulae Ia, Ib and III are independently selected from H and $C_{1-6}$alkyl.

9. The method according to claim 8, wherein $R^2$ to $R^6$ in the compounds of the formulae Ia, Ib and III are independently selected from H and methyl.

10. The method according to claim 1, wherein the optional substituents on $R^2$ and $R^6$ in the compounds of the formulae Ia, Ib and III are independently selected from one or more of OH, halo, CN, $NO_2$, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, aryl, aryloxy, aryl($C_{1-4}$alkoxy), heteroaryl, heteroaryloxy, heteroaryl($C_{1-4}$alkoxy), $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

11. The method according to claim 1, wherein the method is performed in the presence of ammonia.

12. The method according to claim 1, wherein the method is performed in the presence of an ammonia equivalent of the formula $NH_4^+X^-$, in which X is selected from halo, $R^9COO$, $R^9SO_4$ and $BF_4$ and in which $R^9$ is selected from $C_{1-10}$alkyl, $C_{3-20}$cycloalkyl, aryl and heteroaryl, all of which are optionally substituted.

13. The method according to claim 12, wherein X is Cl or Br.

14. The method according to claim 13, wherein the optional substituents on $R^9$ are independently selected from one or more of OH, halo, CN, $NO_2$, phenyl, benzyl, $C_{1-6}$alkoxy, halo-substituted $C_{1-6}$alkoxy, $C_{1-6}$alkyl, halo-substituted alkyl, $C_{2-6}$alkenyl, $C_{2-6}$alkenyloxy, $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

15. The method according to claim 1, wherein the method is performed in a solvent.

16. The method according to claim 15, wherein the solvent is selected from methanol, ethanol, propanol, butanol, toluene, tetrahydrofuran, acetonitrile, benzene, dioxane, methylene chloride, liquid ammonia, ionic liquids and mixtures thereof.

17. The method according to claim 16, wherein the solvent is methanol.

18. The method according to claim 1, wherein the method is performed at a temperature of from −40° C. to +100° C.

19. The method according to claim 18, wherein the method is performed at room temperature.

20. The method according to claim 1, wherein the method is performed in the presence of a catalyst.

21. The method according to claim 20, wherein the catalyst is a transition metal catalyst.

22. The method according to claim 21, wherein the metal is selected from rhodium, ruthenium, iridium, copper, platinum, palladium and nickel.

23. The method according to claim 22, wherein the metal is rhodium.

24. The method according to claim 20, wherein the catalyst comprises a chiral or achiral ligand.

25. The method according to claim 24, wherein the chiral ligand is a phosphine, diphosphine, aminophosphine, amine, carbene or oxazoline.

26. The method according to claim 24, wherein in the compounds of formula III, $R^2$ and $R^3$ are different and enantiomerically enriched compounds of formulae Ia and/or Ib are prepared.

27. The method according to claim 1, wherein when $R^2$ and $R^3$ are different in compounds of the formulae Ia and/or Ib, the method further comprises chirally resolving the compounds of formulae Ia and/or Ib.

28. The method according to claim 27, wherein the chiral resolution comprises diastereomeric ester formation or diastereomeric salt formation.

29. The method according to claim 28, wherein the method further comprises separating the diastereomers using crystallization or chromatography.

* * * * *